United States Patent
Wang et al.

(10) Patent No.: US 7,295,724 B2
(45) Date of Patent: Nov. 13, 2007

(54) POLYMER BASED DISTRIBUTIVE WAVEGUIDE SENSOR FOR PRESSURE AND SHEAR MEASUREMENT

(75) Inventors: Wei-Chih Wang, Sammamish, WA (US); Per G. Reinhall, Seattle, WA (US)

(73) Assignee: University of Washington, Seattle, WA (US)

( * ) Notice: Subject to any disclaimer, the term of this patent is extended or adjusted under 35 U.S.C. 154(b) by 21 days.

(21) Appl. No.: 11/068,938

(22) Filed: Feb. 28, 2005

(65) Prior Publication Data

US 2005/0232532 A1    Oct. 20, 2005

Related U.S. Application Data

(60) Provisional application No. 60/548,965, filed on Mar. 1, 2004.

(51) Int. Cl.
*G02B 6/00* (2006.01)

(52) U.S. Cl. .......................................... 385/13; 385/37

(58) Field of Classification Search .................. 385/13, 385/37

See application file for complete search history.

(56) References Cited

U.S. PATENT DOCUMENTS

| | | | |
|---|---|---|---|
| 4,295,738 A | | 10/1981 | Meltz et al. |
| 4,761,073 A | | 8/1988 | Meltz et al. |
| 5,760,391 A | * | 6/1998 | Narendran ............. 250/227.14 |
| 6,110,592 A | * | 8/2000 | Grizante et al. ............ 428/375 |
| 6,185,020 B1 | * | 2/2001 | Horiuchi et al. ............... 398/31 |
| 6,571,027 B2 | * | 5/2003 | Cooper et al. ................ 385/12 |
| 6,702,858 B2 | | 3/2004 | Christensen | |

FOREIGN PATENT DOCUMENTS

| WO | WO 03/076887 A1 | 9/2003 |
|---|---|---|
| WO | PCT/US2005/006746 | 6/2005 |

* cited by examiner

*Primary Examiner*—Ellen E. Kim
(74) *Attorney, Agent, or Firm*—Blakely Sokoloff Taylor & Zafman LLP

(57) ABSTRACT

According to embodiments of the present invention, a distributed pressure and shear stress sensor includes a flexible substrate, such as PDMS, with a waveguide formed thereon. Along the waveguide path are several Bragg gratings. Each Bragg grating has a characteristic Bragg wavelength that shifts in response to an applied load due to elongation/compression of the grating. The wavelength shifts are monitored using a single input and a single output for the waveguide to determine the amount of applied pressure on the gratings. To measure shear stress, two flexible substrates with the waveguide and Bragg gratings are placed on top of each other such that the waveguides and gratings are perpendicular to each other. To fabricate the distributive pressure and shear sensor, a unique micro-molding technique is used wherein gratings are stamped into PDMS, for example.

7 Claims, 11 Drawing Sheets

- Silicon
- AZ1350 photoresist
- SU-8 photoresist
- Gratings
- PDMS 1
- PDMS 2
- Opaque PDMS ☐ Silicon
☐ Ultra-i123 photoresist
☐ SU-8 photoresist
▦ Gratings
▨ PDMS 1
☐ PDMS 2
▨ Opaque PDMS

POLYMER BASED DISTRIBUTIVE WAVEGUIDE SENSOR FOR PRESSURE AND SHEAR MEASUREMENT

CROSS REFERENCE TO RELATED APPLICATIONS

This application claims the benefit of U.S. Provisional Application No. 60/548,965, filed Mar. 1, 2004.

BACKGROUND

1. Field

Embodiments of the present invention relate to sensors and, in particular, to pressure and shear sensors.

2. Discussion of Related Art

Investigation in tactile sensing has been an active research area for the past 30 years. The technologies applied to date in the tactile sensing field include metal strain gages, conductive elastomers, carbon fibers, conductivity measurement (usually in association with elastomers), ferroelectric polymers (i.e., $PVF_2$), semiconductor strain gages, magnetostriction, capacitance and optoelectronics. The characteristics of all tactile sensors depend, to some degree, on the properties of the deformable contact material. Each material has its advantages and disadvantages, depending on physical properties and manufacturing concerns. Conventional metal strain gages, for example, measure strain based on the induced resistance change. Strain may be defined as the amount of change in length divided by the original length ($\Delta l/l$) The advantage of metal strain gages is that they are inexpensive, commonly used in industry, and they have a wide range of sensitivity. The disadvantages of metal strain gages in the use of measuring skin tractions are that they are not suitable for large deformation applications and that the gage factors are too small (two to four for platinum and −12 to −20 for nickel) yielding a low sensitivity. In addition, these gages are not suitable for use in arrays since they would require a large amount of supporting circuits and specific interconnecting wires.

Semiconductor strain gages, however, can measure very small strains (~1 µm/m) and have a very high gage factor (>150 for Ge and n-type Si). The most widely used semiconductor gages are piezoresistive based silicon devices. These sensors have a very linear mechanical and electrical response almost free of any noticeable hysteresis effect. They also have a relatively low thermal expansion coefficient ($Si=3.5 \times 10^{-6}/°C$.) compared to metals. The disadvantages include its breaking stress (ranging from 0.41-2.1 giga Pascals (GPa), depending on the diameter of the deformable element). Stress may be defined as total force divided by area (f/A). The devices are relatively stiff (Young's modulus around 130 GPa), and can handle a maximum strain around 0.5%. These devices are therefore mainly for micro strain measurements, and are not intended for large deflections. Thus, the use of an array of silicon sensors for measuring skin tractions is not feasible.

Piezoelectric materials are also commonly used for strain/stress measurement. A piezoelectric material generates an electrical charge when subjected to mechanical stress. The most widely used piezoelectric materials are electric polymers, such as polyvinylidene difluoride (PVDF or $PVF_2$). The advantage of using $PVF_2$ film is that it is flexible and can withstand rather large strains without severe deterioration. Films can be manufactured in thickness ranging from a few microns to a few millimeters. However, the material is structurally weak and prone to damage. In addition, the material suffers from poor fatigue life and from shrinkage due to aging and temperature.

Conductive elastomers are another type of polymer that can be made electrically active either by the addition of metallic compounds or by formation in the presence of high electric fields. These materials offer high resiliency and resistance to corrosion. However, they are highly nonlinear in their electrical and mechanical response and are often mechanically and thermally unstable. Examples include carbon-filled liquid silicone rubber and the conductive polymer in the commercially available F-SCAN force sensitive resistor (TekScan, Inc., Boston, Mass.). The principle of the F-SCAN sensor is based on the fact that the resistance between two intersection points of two conductive polyester sheets is sensitive to contact force. This type of sensor can only be used in special circumstances because of its nonlinear response, hysteresis, and gradual voltage drift.

Another means of transducing force is the use of optical fiber. Optical sensors are unaffected by electromagnetic field interference and can be made relatively compact with a diode source and detector. Optical sensors are also known for their sensitivity and high dynamic range. Furthermore, the sensors can be embedded in most structures with minimal modification. The optical sensors do not suffer from hysteresis and drift, and their response tends to be highly linear. However, there are no available optical sensors that can be used to measure distribution of pressure and shear over a surface. Current optical sensors all use a single optical fiber and are intended for single point measurement of strain or pressure.

There are currently no flexible high-resolution sensors capable of measuring the distribution of both shear and pressure at the plantar interface. As mentioned earlier, one method to measure shear at point locations is to use magneto-resistive transducer disks (16 mm in diameter and 3 mm thick) mounted in an insole that is directly placed under three critical stress regions under a foot (e.g. heel, first and third metatarsals). The sensor's resistance varies with the strength of magnetic field in which it is placed. Lateral movement corresponding to shear force can be monitored by the movement of a magnet that is placed centrally above a center tapped magneto resistor in a bridge configuration.

A piezoelectric film-based sensor using copolymer PVdf-TrFE has also been studied. Again the sensors are few in number and are placed only in critical locations. No shear distribution over the plantar interface can be measured using this sensor. More recently there are developments in distributive shear and pressure sensors using an integrated capacitive sensor and a strain gage sensor.

For the capacitive sensor, one of the problems is its susceptibility to electrical interference because of its high impedance. Strain gages, on the other hand, require additional structure to extract the shear component. Both designs suffer from low spatial resolution, drift, and a high sensitivity to temperature. Another severe limitation is that compliance of these sensors is not commensurate with skin when configured to measure shear. This makes them unsuitable for use as in-shoe shear sensors as they will affect the stresses they are intended to measure. In order to address these challenges, we propose to develop a novel means of transducing plantar pressure and shear stress using a distributive Bragg grating based polymeric waveguide sensor array.

SUMMARY OF EMBODIMENTS OF THE INVENTION

In embodiments of the present invention, an apparatus is defined for providing measurement of pressure and/or shear stress over an area using a flexible polymer-based Bragg grating sensor. This sensor may be an innovative use of existing waveguide technology and micro-electromechanical system (MEMS) fabrication techniques. The sensor may have high spatial resolution and be able to conform to and be embedded into a structure of interest. Using Bragg grating technology will allow collection of data from a large number of pressure points within the sensor using only a small number of input and output channels. By using highly compliant silicone rubber as the optical waveguide, the sensor system may be able to conform to the structure of interest. Polymer materials used here are biocompatible (i.e. silicone rubber) and have a mechanical impedance to the plantar soft tissue.

In one embodiment, a pressure sensor includes a flexible substrate. A waveguide may be disposed in or on the flexible substrate. The waveguide may include an input to receive an optical signal and an output to detect a reflected or transmitted optical signal. The pressure sensor also may include a Bragg grating array. The Bragg grating array may include Bragg gratings disposed in series along the length of the waveguide. Each Bragg grating may include a different characteristic grating spacing and thus reflect a different Bragg wavelength.

In an alternative embodiment, a shear sensor includes a first sensor disposed in or on a first flexible substrate and a first detector array disposed in or on the first flexible substrate along a first series path. The first series path may include a first input and a first output. The shear sensor also includes a second sensor having a second flexible substrate and a second detector array disposed in or on the second flexible substrate along a second series path. The second series path may include a second input and a second output. The first sensor may be disposed on the second sensor and the first series path may be disposed perpendicular to the second series path.

In one embodiment, a light beam may be passed through the first waveguide. The first Bragg grating and the second Bragg grating may be deformed in response to a load being applied orthogonal to the surface of the first flexible substrate. The output of the first waveguide may be monitoring to detect a shift in the first Bragg wavelength and a shift in the second Bragg wavelength to determine an amount of deformation of the first and second Bragg gratings.

In an alternative embodiment, a second light beam may be passed through the second waveguide. The third Bragg grating and the fourth Bragg grating may be deformed in response to a load being applied orthogonal to the surface of the second flexible substrate. The output of the first and second waveguides may be monitoring to detect a shift in the first, second, third, and fourth Bragg wavelengths to determine an amount of shear stress.

In an alternative embodiment, a light detector disposed in or on the flexible substrate and coupled to the waveguide output, the light detector to detect light transmitted by the Bragg gratings, wherein the change in wavelength content of light transmitted by a particular Bragg grating is determined by the grating spacing of the particular Bragg grating.

In one embodiment, at least one Bragg grating may reflect a second wavelength different from its characteristic wavelength corresponding to the original grating spacing in response to the change grating spacing. In an alternative embodiment, at least two Bragg gratings are to transmit a second wavelength from its characteristic wavelength content corresponding to the original grating spacing in response to the change grating spacing.

In one embodiment, a light detector may be disposed in or on the flexible substrate and coupled to the waveguide output. The light detector may detect light transmitted by the Bragg gratings. Change in wavelength content of light transmitted by a particular Bragg grating may be determined by the grating spacing of the particular Bragg grating. A wavelength shift detector disposed in or on the flexible substrate and coupled to the waveguide output may detect the second wavelength content and determine an amount of shift from the characteristic wavelength content to the second wavelength content. Two couplers may be disposed in or the flexible substrate. One coupler may couple the transmitted optical signal from the light source to the waveguide and the other coupler may couple the reflected optical signal to the wavelength content shift detector/light detector from the waveguide. A time domain multiplexer (TDM) may be coupled to the wavelength content shift detector. The TDM may separate the transmitted optical signal of one Bragg grating from the reflected optical signal of another Bragg grating by a time delay.

BRIEF DESCRIPTION OF THE DRAWINGS

In the drawings, like reference numbers generally indicate identical, functionally similar, and/or structurally equivalent elements. The drawing in which an element first appears is indicated by the leftmost digit(s) in the reference number, in which.

DETAILED DESCRIPTION OF THE ILLUSTRATED EMBODIMENTS

Figure 1:
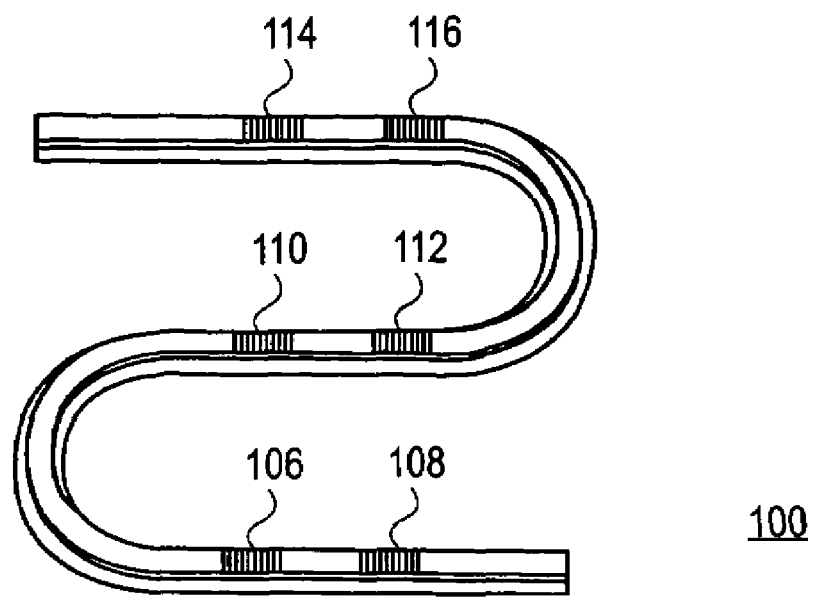
FIG. 1 is a perspective diagram of a distributive pressure sensor 100 according to an embodiment of the present invention

FIG. 1 is a perspective diagram of a distributive pressure sensor 100 according to an embodiment of the present invention. In the illustrated embodiment, distributive sensing is accomplished using Bragg gratings disposed along a single waveguide path having a single input and a single output for measurement. For example, in the illustrated embodiment, the pressure sensor 100 includes a flexible material 102. A waveguide 104 is disposed in or on the flexible material 102. Several Bragg gratings 106, 108, 110, 112, 114, and 116 are formed in or on the waveguide 104. Although a single waveguide 104 is illustrated as being disposed in or on the flexible material 102, in other embodiments of the present invention more than a single waveguide may be disposed in or on the flexible material 102.

In embodiments of the present invention, the flexible material 102 may be any suitable flexible optical medium capable of having a waveguide, Bragg gratings, and terminals formed therein or thereon. In one embodiment, the flexible material 102 may be a polydimethylsiloxane (PDMS) elastomer. In other embodiments, the flexible material 102 may be any suitable polymer such as an acrylic-based polymer, Mylar®, a photoresist type of polymer, poly(methyl methacrylate) (i.e., Plexiglas®), an epoxy based polymer, or the like.

In embodiments of the present invention, the waveguide 104 may be capable of receiving a light beam, directing the light beam to the gratings 106, 108, 110, 112, 114, and 116, and away from the gratings 106, 108, 110, 112, 114, and 116.

In embodiments of the present invention, the gratings 106, 108, 110, 112, 114, and 116 are encoded to reflect light of specific Bragg wavelengths $\lambda_B$ in response to an incident light beam. The specific Bragg wavelength $\lambda_B$ may be represented by $\lambda_B=2n\Lambda$, where n is the index of refraction of the core of the waveguide 104 and $\Lambda$ is the spacing or pitch of the particular grating. In one embodiment, the grating 106 may be encoded to reflect $\lambda_1$ when not under an applied load, the grating 108 may be encoded to reflect $\lambda_2$ when not under an applied load, the grating 110 may be encoded to reflect $\lambda_3$ when not under an applied load, the grating 112 may be encoded to reflect $\lambda_4$ when not under an applied load, the grating 114 may be encoded to reflect $\lambda_5$ when not under an applied load, and the grating 116 may be encoded to reflect $\lambda_6$ when not under an applied load.

Figure 2:
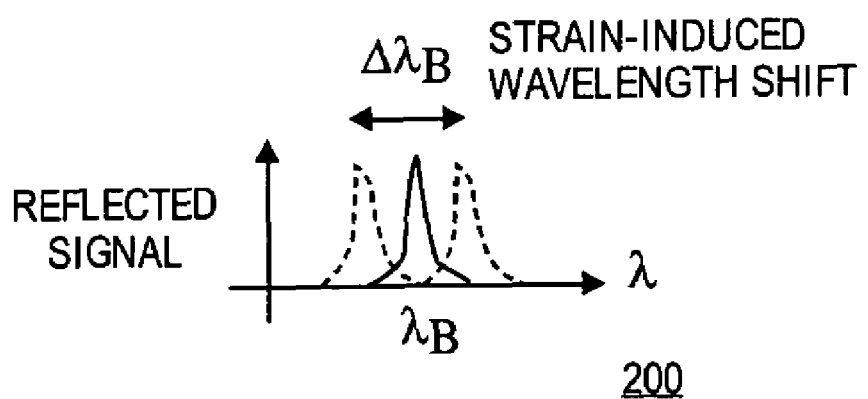
FIG. 2 is a graphical representation illustrating strain-induced Bragg wavelength shift $\Delta\lambda_B$ for a Bragg grating according to an embodiment of the present invention.

If a grating is under an applied load, the specific Bragg wavelengths $\lambda_B$ may deviate in response to the strain caused by the applied load. In embodiments, the range of specific Bragg wavelengths $\lambda_B$ that one grating may reflect does not overlap with the range of specific Bragg wavelengths $\lambda_B$ that another grating may reflect. Thus, the gratings 106, 108, 110, 112, 114, and 116 may each reflect a different range of Bragg wavelengths $\lambda_B$. FIG. 2 is a graphical representation 200 illustrating strain-induced Bragg wavelength shift $\Delta\lambda_B$ for a grating according to an embodiment of the present invention.

Figure 3:
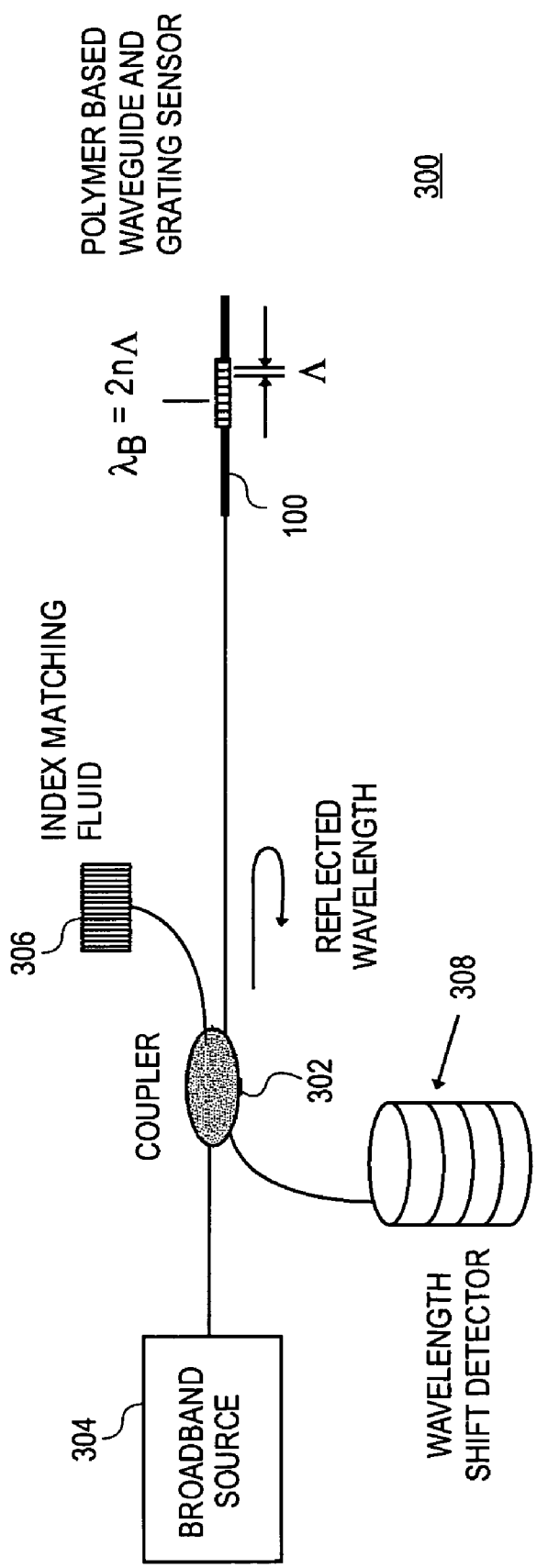
FIG. 3 is a schematic diagram of a pressure sensor implementing a wavelength division multiplexing (WDM) Bragg grating sensor configuration according to an alternative embodiment.
Figure 4:
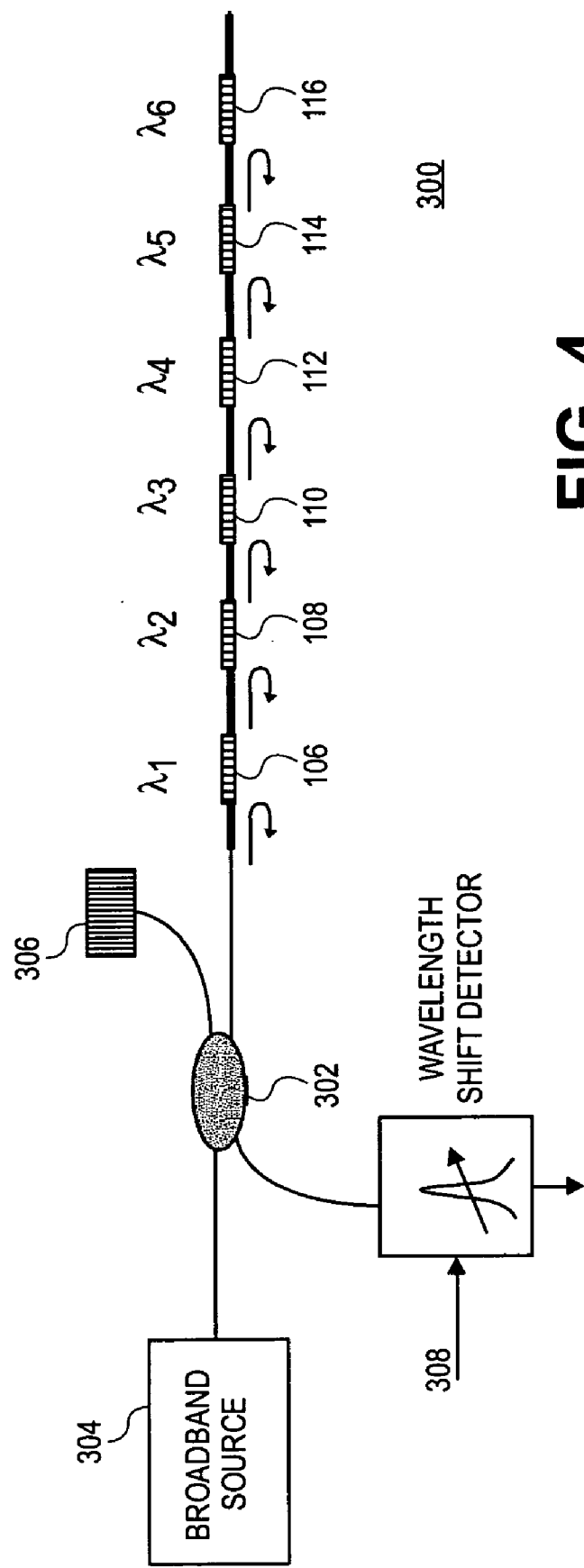
FIG. 4 is a schematic diagram of the pressure sensor depicted in FIG. 3 according to an alternative embodiment.

FIGS. 3 and 4 are schematic diagrams of a pressure sensor 300 according to an alternative embodiment in which the pressure sensor 100 is coupled to a coupler 302. In the illustrated embodiment, the coupler 302 is coupled to a broadband light source 304, index matching fluid 306, and a wavelength shift detector is disposed in or on the flexible material 102. In this embodiment, the advantage is that all the gratings 106, 108, 110, 112, 114, and 116 are connected in series to each other in the waveguide 104 so that there is a single path from a light source to a light detector. In alternative embodiments, the coupler 302, the broadband light source 304, and/or the wavelength shift detector may be located in or on the pressure sensor 100, that is, embedded in the flexible material 102. Although a light source 304 is illustrated as being disposed in or on the flexible material 102, in other embodiments of the present invention more than a single light source may be disposed in or on the flexible material 102.

In embodiments of the present invention, the coupler 302 may be any suitable 2×2 bidirectional coupler that is capable of coupling light into and out of the pressure sensor 100.

In embodiments of the present invention, the broadband light source 304 may be any suitable light source capable of transmitting a light beam having a broad range of wavelengths. In one embodiment, the broadband light source 304 may provide ultraviolet (UV), visible, or infrared band of light using laser diode or light emitting diode. In another embodiment, the broadband light source 304 may provide white light.

In embodiments of the present invention, the index matching fluid 306 may be any suitable index matching material that is capable of matching the index of refraction n of the coupler 302 with the index of refraction n of the flexible material 102.

In embodiments of the present invention, the wavelength shift detector 308 may be any suitable light detector capable of determining light wavelengths. In embodiments in which the wavelength shift detector 308 may be located off of the flexible material 102, the wavelength shift detector 308 may be a spectrum analyzer.

In the illustrated embodiment, the coupler 302 couples a broadband light beam from the broadband light source 304 to the gratings 106, 108, 110, 112, 114, and 116 on the pressure sensor 100. Each of the gratings 106, 108, 110, 112, 114, and 116 may reflect light having its specific Bragg wavelength $\lambda_B$ back to the coupler 302. The coupler 302 directs the reflected light to the wavelength shift detector 308, which determines the Bragg wavelength $\lambda_B$ reflected by the gratings 106, 108, 110, 112, 114, and 116.

Alternative embodiments of the present invention not only include at least one waveguide 104 disposed in or on the flexible substrate 102 to detect light reflected from the Bragg gratings 106, 108, 110, 112, 114, and 116, but also to detect transmitted light. For example, the detected transmitted light may be the light having a wavelength that misses the Bragg wavelength of the particular grating 106, 108, 110, 112, 114, or 116. In these embodiments, the output of the waveguide 104 may be at the same physical location as the input of the waveguide 104, and it may be possible to detect deformation using transmitted light. Thus, and embodiments of the present invention are not limited to detection of deformation using reflected light. Embodiments of the invention may detect deformation using reflected light, transmitted light, and/or a combination of reflected light and transmitted light.

In embodiments of the present invention, each of the gratings 106, 108, 110, 112, 114, and 116 serves as a pressure point. In one embodiment, the broadband light source 304 may transmit a light beam to the waveguide 104 through the coupler 302. The gratings 106, 108, 110, 112, 114, and 116 may reflect their specific Bragg wavelengths $\lambda_B$ in response to the incident light beam. If a vertical load is applied to the flexible material 102, one or more of the gratings 106, 108, 110, 112, 114, and 116 may become deformed. For example, suppose that a vertical load is applied between the grating 106 and the grating 108. The pitches of the gratings 106 and 108 may become elongated due to a Poisson's ratio deformation orthogonal to the applied loading. In this embodiment, the specific Bragg wavelengths $\lambda_B$ reflected by the gratings 106 and 106 may shift upwards from the no-load specific Bragg wavelengths $\lambda_B$.

In one embodiment, the wavelength shift detector 308 may monitor the wavelength shifts and a map of pressure may be constructed based the wavelength shifts and the deformation of each pressure point is determined by monitoring the shift in Bragg wavelengths $\lambda_B$ of the reflected signals with the changes in the measured in each grating 106, 108, 110, 112, 114, and 116. In our case, the measured is the strain induced by the load on each grating 106, 108, 110, 112, 114, and 116.

The Bragg wavelength $\lambda_B$ may shift with changes in either the index of refraction n or the grating spacing/pitch $\Lambda$. The strain response arises due to both physical elongation (corresponding fractional change in grating pitches) and the change in index of refraction n as a result of the photoelastic effect, or due to the temperature dependence of the index of refraction n. The differential change in the Bragg wavelength $\lambda_B$ resulting from an applied strain field and temperature change is given in A. D. Kersey, M. A. Davis, H. J. Patrick, M. Leblanc, K. P. Koo, C. G. Askins, M. A. Putmand, and E. J. Friebele, "Fiber grating sensors," J. of Lightwave Technol. 15 (8), p. 1442-1462, 1997) as:

$$\Delta\lambda_B = 2n\Lambda\left[\varepsilon_{zz}\left(1-\left(\frac{n^2}{2}\right)(\rho_{12}-v(\rho_{11}+\rho_{12}))\right)+\left(\alpha+\frac{\left(\frac{dn}{dT}\right)}{n}\right)\Delta T\right]$$

where $\rho_{ij}$ are Pockel's coefficients of the stress-optic tensor, $v$ is poison's ratio, $\varepsilon_{zz}$ is the longitudinal strain and $\alpha$ is the coefficient of thermal expansion of the waveguide 104, and $\Delta T$ is the temperature change. It may not be possible to separate the effect of the temperature from the effect of the strain with only one grating.

For the wavelength shift detection, an optical fiber based Fabry-Perot (FP) scanning interferometer may be used. In one embodiment, optical fiber based Fabry-Perot (FP) scanning interferometer may include two mirrors directly deposited to the ends of an optical fiber to form an optical cavity. Wavelength scanning may be achieved by axially straining a short section of the fiber by a piezoelectric actuator. As the optical fiber based Fabry-Perot (FP) scanning interferometer scans over the returning signals from the gratings 106, 108, 110, 112, 114, and 116, the Bragg wavelengths $\lambda_B$ are determined and recorded from the voltage applied to the piezoelectric actuator as the return signals are detected. The phase modulation ($\Delta\phi$) induced by the Bragg wavelength shift, $\Delta\lambda_B$, is given by $\Delta\Phi=2\pi n_f d\Delta\lambda_B/\lambda_B^2$, where $n_f$ refraction of the fiber and d is the fiber cavity length.

In an alternative embodiment, an integrated electro-optic (EO) waveguide based Fabry-Perot (FP) scanning interferometer may be used. The phase modulation may be done by electro-optical means. The refractive index change $\Delta n(x, y, z)$ due to an applied voltage, V, in the small electrode gap region is equal to $\Delta n=n^3\gamma_{33}kV$, where n is the electro-optic (EO) refractive index, $\gamma_{33}$ is the electro-optic coefficient for the core structure, k is the proportionality constant which depends on the overlap factor of the voltage-induced applied electric field and the guided optical mode profile. The phase modulation ($\Delta\phi$) induced by the voltage induced index change is given by, $\Delta\Phi=2\pi\Delta n_f/\lambda$, where $n_f$ is index of refraction of the fiber and d is the fiber cavity length.

In an alternative embodiment, an off-the-shelf fiber Bragg grating interrogation system may be used. Currently available Fabry-Perot scanners can be scanned at rates >300 Hz. The minimum resolvable Bragg wavelength shift, $\Delta\lambda_B$ for a free spectral range of forty nm (wavelength range 1525 to 1565 nm) with grating spaced by 625 pm via a sixteen bit digital to analog is around 0.6 pm, which should be sufficient to provide the speed and resolution needed for dynamic strain measurement of stress distributions.

Although for simplicity only six Bragg gratings are shown in the pressure sensor 100, in embodiment of the present invention, ten to twenty Bragg gratings may be used in one sensor array, as described in A. D. Kersey, M. A. Davis, H. J. Patrick, M. Leblanc, K. P. koo, C. G. Askins, M. A. Putmand, and E. J. Friebele, "Fiber grating sensors," J. of Lightwave Technol. 15 (8), p. 1442-1462, 1997]. A system made by Micron Optics Inc. states that a sixty-three-element Bragg grating array is possible on their Bragg gating interrogated system. However, in embodiments of the present invention, greater numbers of sensors may be needed.

In order to significantly increase the number of multiplexed Bragg gratings, a hybrid of time domain multiplexing (TDM) and wavelength division multiplexing (WDM) techniques may be used. A 3×3 fiber grating array has been successfully demonstrated earlier by Berkoff in T. A. Berkoff et al., "Hybrid time and a wavelength division multiplexed fiber grating array," Prof. SPIE, vol. SPIE-2444, p. 288, 1995, which is incorporated herein by reference in its entirety.

Figure 5:
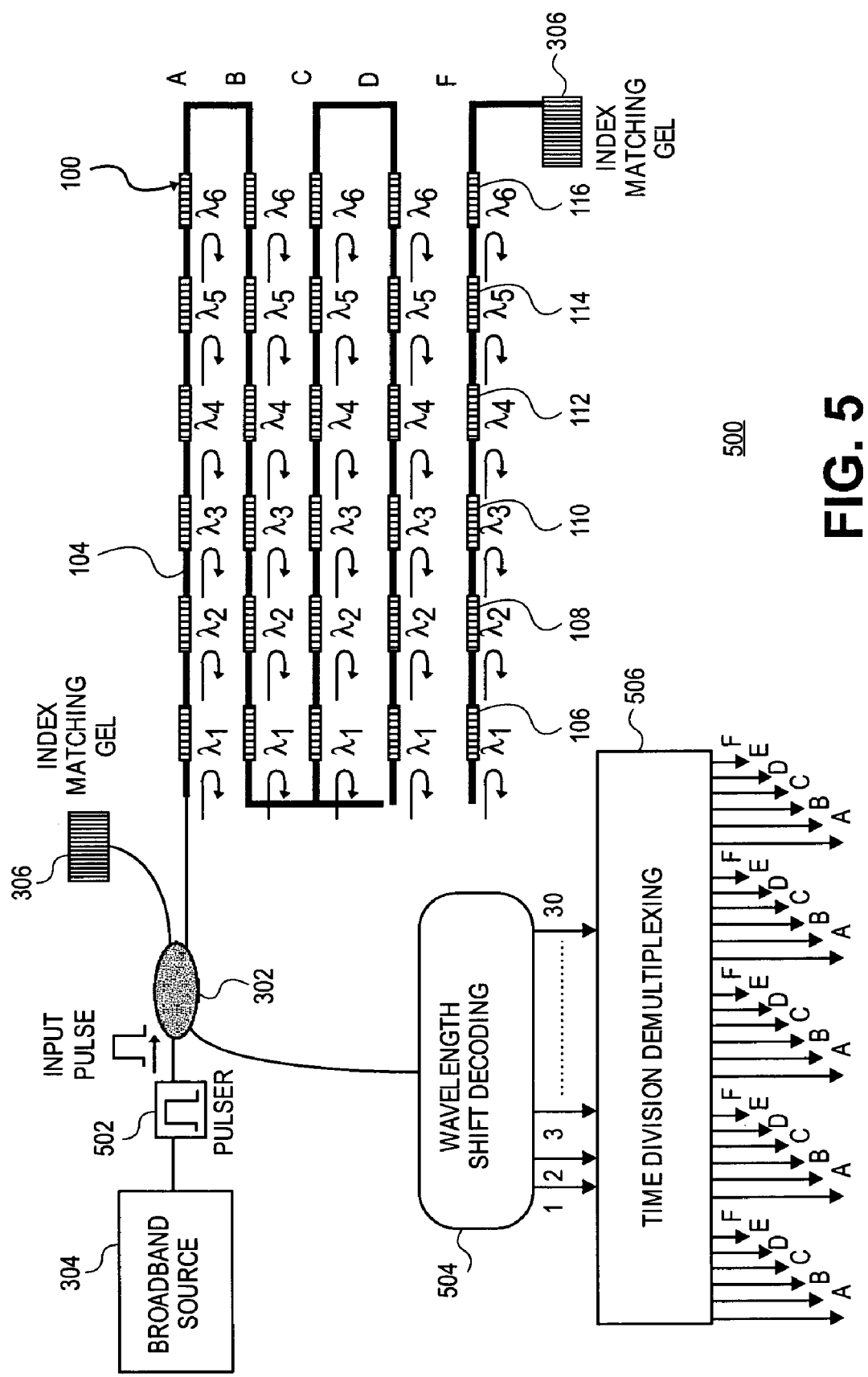
FIG. 5 is a schematic diagram illustrating time domain multiplexing (TDM) and wavelength division multiplexing (WDM) of a pressure sensor according to an embodiment of the present invention final pressure/shear sensor layout according to an embodiment of the present invention.

FIG. 5 is a schematic diagram illustrating time domain multiplexing (TDM) and wavelength division multiplexing (WDM) of a pressure sensor 500 according to an embodiment of the present invention. The pressure sensor 500 includes the coupler 302, the broadband light source 304, and the pressure sensor 100. The illustrated pressure sensor 500 also includes a pulser 502 coupled between the broadband light source 304 and the coupler 302, a wavelength shift decoder 504 coupled to the coupler 302, and a time division demultiplexer 506 coupled to the wavelength shift decoder 504.

In time domain multiplexing, the response from each grating 106, 108, 110, 112, 114, and 116 may be separated from another by a time delay due to the length separating two gratings. By operating within the limit of the wavelength shift decoder 504, the same wavelength division is reused, each placed at a greater distance along the waveguide 104. In the illustrated embodiment, the letters A, B, C, D, etc., represent row numbers of the grating sensor array 100 and the numbers 1, 2, 3, 4 . . . N represent the different gratings within the grating sensor array 100 and their different wavelengths. The wavelength shift decoding in 504 may be performed by the wavelength shift detector 308 in FIG. 3. The arrows in FIG. 5 represent the waves reflected by the gratings 106, 108, 110, 112, 114, and 116.

One of the advantages of pressure sensors implemented according to embodiments of the present invention is that a large number of gratings may be integrated along a single waveguide for distributive sensing. Pressure sensors implemented according to embodiments of the present invention also have an advantage over intensity-based sensors in the self-referencing nature of its output. Unlike intensity-based sensors, which depend on the source power and losses in the connecting fibers and couplers, the sensing information of pressure sensors implemented according to embodiments of the present invention is encoded directly into the wavelengths of light used. This wavelength-encoded nature makes wavelength division multiplexing possible by allowing each grating to be allocated with a section of the broadband light source spectrum.

Other advantages are that the flexible distributed pressure and shear sensor have thin profiles, are simple to make and cost-effective, and have no moving parts In order to increase the resolution of the distributed optical sensor, a large array of gratings must be manufactured in the system. Difficulties lie in the consistent and accurate manufacturing of these devices. To solve this problem, we propose a batch process for the sensor construction similar to that of integrated circuit fabrication.

Techniques involved sensor developments are laser-beam etching, micro-molding, electron-beam writing and holographic interference exposure processes. These approaches reduce the fabrication complexity, while improving the signal to noise ratio and image resolution. Batch processing also guarantees a consistent product, low cost in manufacturing and makes mass production possible. The batch fabrication process, which involves an injection molding technique with polydimethylsiloxane (PDMS) as the optical medium, also is a unique fabrication process for pressure sensors implemented according to embodiments of the present invention.

Figure 6:
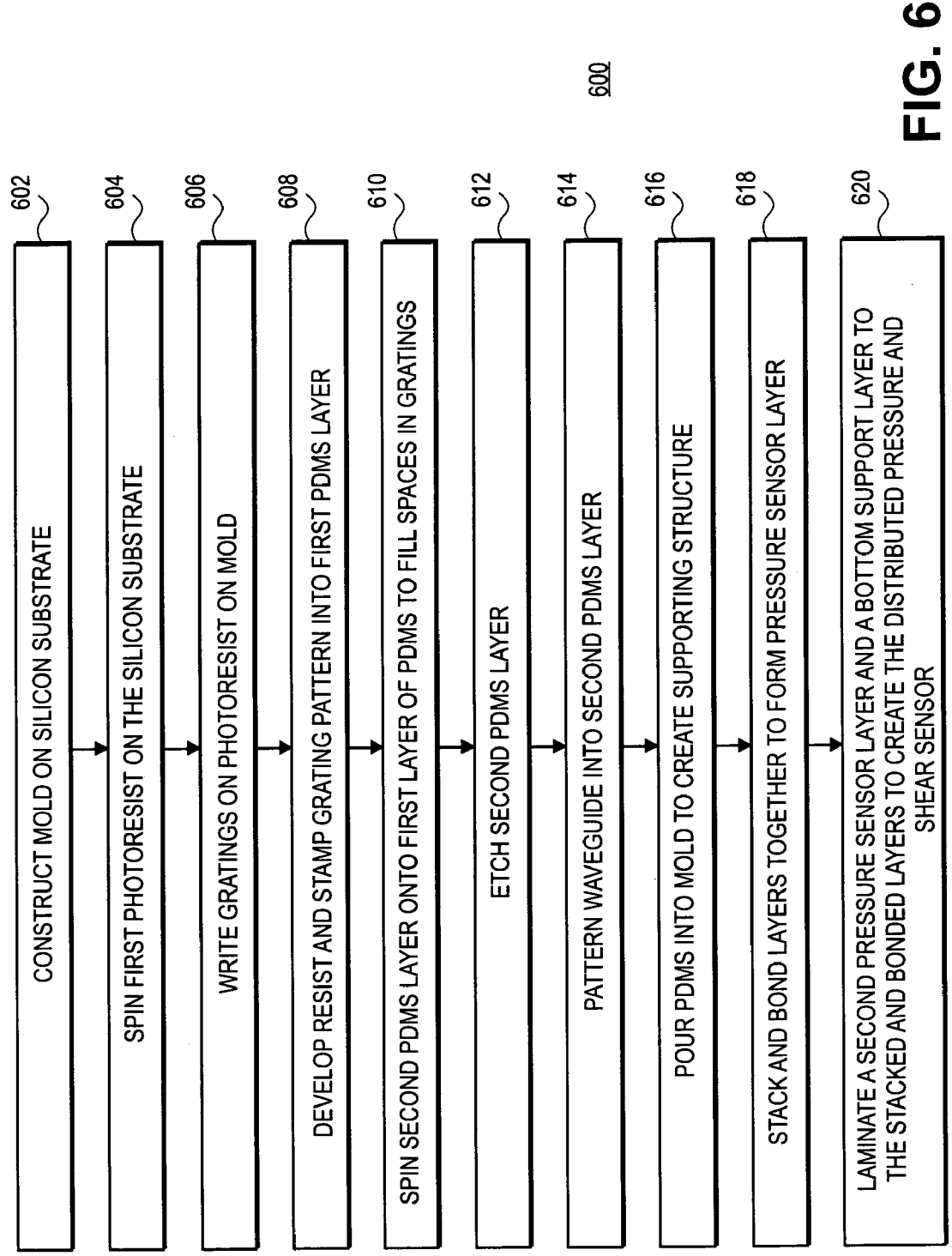
FIG. 6 is a flowchart illustrating a process for fabricating a pressure sensor and a shear sensor according to an embodiment of the present invention.

FIG. 6 is a flowchart illustrating a process 600 for fabricating a pressure sensor and a shear sensor according to an embodiment of the present invention. FIG. 7 is a cross-section view of stages of fabrication of a pressure sensor and a shear sensor using the process 600 according to an embodiment of the present invention. In embodiments of the present invention, a single layer of the pressure sensor 100 is used for pressure sensing. When a force is applied between two gratings in the x direction, one of the gratings will be under compression and the other will be under (tension) elongation. Pressure is measured in the x-z plane. Two layers of the pressure sensor 100 are used for shear sensing. To determine pressure in the x-y plane, you use the second flexible layer on top of the first layer so that the gratings on the first and second layers are orthogonal to each other. A three-dimensional analysis of the pressure and shear sensor may be determined using the x-y plane information and the x-z plane information.

Waveguides and gratings may be constructed using PDMS elastomer, which is widely available, clean room compatible, and a physically and chemically stable silicone rubber with a wide range of applications. Sylgard 180 series silicone elastomers from Dow-Corning Corporation are among the most commonly used PDMS elastomers.

The primary advantages of PDMS are that it bonds easily and has very good optical properties such as high transparency, low loss and, most importantly, a refractive index (n=1.43) that closely matches the indices of commercially available optical fibers. Some physical and chemical attributes of PDMS are, compared to other polymers, a unique flexibility (the shear modulus G between 100 kPa and 3 MPa), low durometer hardness (Shore A 40), very low loss tangent (tan $\delta$<<0.001), high gas permeability, low temperature variation, and it is virtually inert to most chemicals and essentially non-toxic in nature. PDMS is also a fairly low cost material ($80/kg).

The primary use for PDMS is usually in providing an elastomeric stamp or mold in soft lithography. However, due to its unique optical and physical properties and low surface energy (~21.6 dyn/cm), which allows replicas to be separated from their molds easily, PDMS is the material of choice for sensors fabricated according to embodiments of the present invention.

In embodiments of the present invention, a simple microfabrication technique is used that allows the rapid construction of sensor systems. In one embodiment, the sensor system may be fabricated using a technique derived from the micro-molding method. The process allows for stacking of many thin patterned PDMS layers to realize a complex 3-D structure. The master for each layer is formed on a silicon wafer using Ultra123 photoresist (Shipley Company, Marlborough, Mass.) or epoxy based SU-8 photoresist (MicroChem Corporation XP SU-8 2000 series, Newton, Mass.) or any deep UV photoresists. PDMS is cast against the master to produce the molded structure.

Figure 7A:
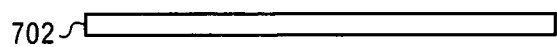
FIG. 7 is a cross-section view of stages of fabrication of a pressure sensor and a shear sensor using the process depicted in FIG. 6 according to embodiments of the present invention.

In a block 602, a mold may be constructed on a silicon substrate 702 (FIG. 7(a)).

Figure 7B:
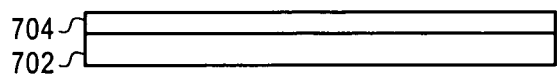

In a block 604, Ultra123 photoresist 704 may be spun on the silicon substrate 702 (FIG. 7(b)).

Figure 7C:
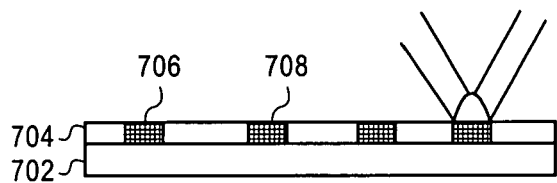

In a block 606, gratings (706, 708, etc.) may then be holographically exposed using a Lloyd's mirror interferometer technique (FIG. 7(c)). In one embodiment, the gratings may be formed by first exposing a 325 nm wavelength UV interference pattern (using a HeCd laser $\lambda$=325 nm) on a photosensitive polymer (Ultra123, refractive index=1.618). The spatial frequency $\nu$ (fringes/mm) may depend on wavelength $\lambda$ and the angle $\phi$ at which the two wave fronts interfere, and may be expressed as $\nu=2 \sin \phi/\lambda$.

In an alternative embodiment, employs electron-beam lithography (EBL) instead of a holographic technique. The advantage of the EBL technique is that both grating and waveguide patterns are directly written onto electron-sensitive polymethylmethacrylate (PMMA) (MicroChem Corporation 495 or 950 series, Newton, Mass.) film on the mold. This procedure will eliminate the need for laser beam etching after release of the first PDMS layer.

Figure 7D:
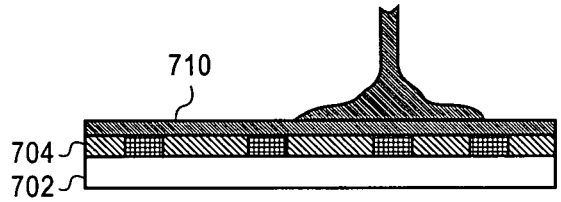

After exposing the photoresist to an UV interference pattern, in a block 608, the resist is developed and the pattern may be transferred (e.g., stamped) to the PDMS 710 using the micro-molding technique (FIG. 7(d)).

Figure 7E:
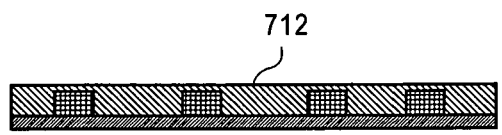

In a block 610, a coating of a slightly different optical index PDMS elastomer 712 may be spun onto the first layer of PDMS 710 until the holes between the gratings are filled with the PDMS 712 (FIG. 7(e)).

Figure 7F:
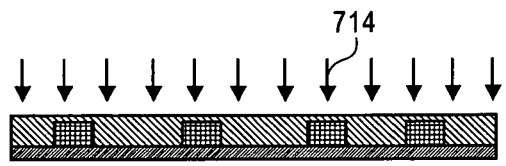

In a block 612, reactive ion etching with argon gas 714 at low pressure (~1 mtorr) may be used to etch down the second PDMS layer (FIG. 7(f)). In one embodiment, etching is performed to reduce the thickness of the second PDMS layer.

Figure 7G:
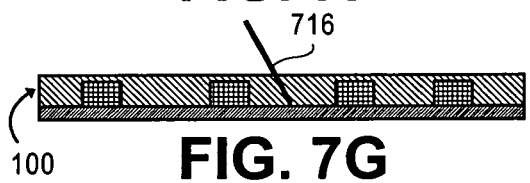
Figure 7H:
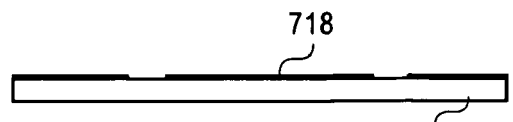

In a block 614, an ultraviolet (UV) laser 716 may be used to pattern the waveguide 104 to create the distributive pressure sensor 100 (FIG. 7(g)).

In one embodiment, the top and bottom supporting structures for a distributive pressure sensor 100 may be fabricated out of opaque PDMS using the same micro-molding technique described in blocks 602-614. The mold of the top supporting layer may be made of another silicon wafer 702 and an epoxy based photoresist 718 (SU-8) (FIG. 7(h)).

Figure 7I:
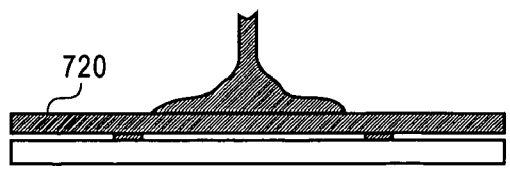
Figure 7J:
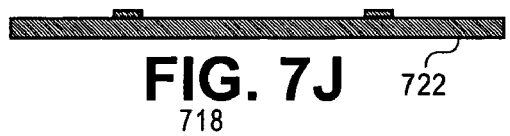
Figure 7K:
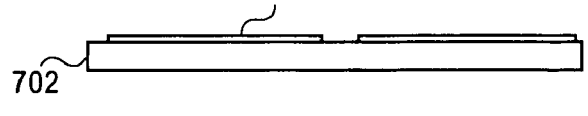
Figure 7L:
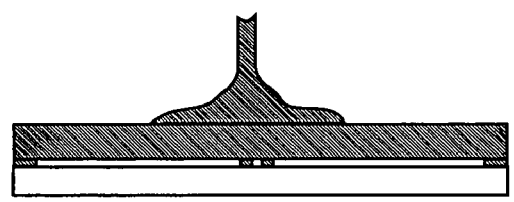
Figure 7M:
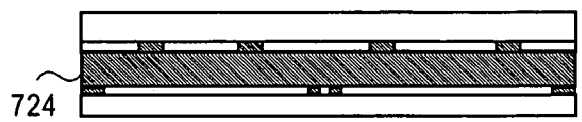
Figure 7N:
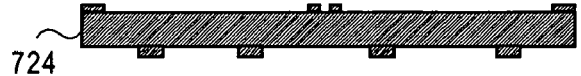

In a block 616, opaque PDMS 720 may be poured into a mold to create the supporting structure 722 (FIGS. 7(i) and 7(j)). The mold of a bottom supporting structure 724 may be made of another silicon wafer 702 and photoresist 718 (FIG. 7(k)) and opaque PDMS 720 may be poured into the second mold (FIG. 7(l)) to create the bottom supporting structure 724 (FIG. 7(m)). The molds are removed from the bottom supporting structure (FIG. 7(n)).

Figure 7O:
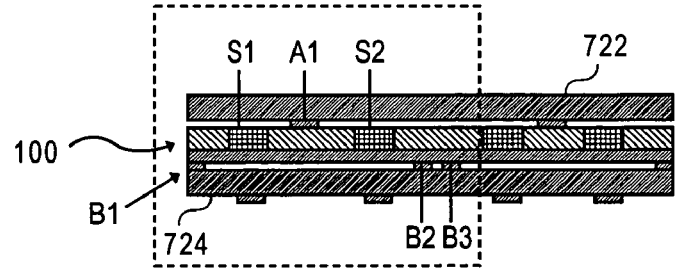

After fabricating the distributive pressure sensor 100, the top support 722, and the bottom support 724, in a block 618, the distributive pressure sensor 100, the top support 722, and the bottom support 724 are stacked and bonded together (FIG. 7(o)) with the distributive pressure sensor 100 disposed between the support structure 722 and the support structure 724.

A vertical load may be transferred to the Bragg gratings in the direction indicated by an arrow 902 through an applicator (A1) bonded between the top support 722 and the distributive pressure sensor 100. The magnitude of the applied pressure is proportional to the sum of the strain obtained by S1 and S2. When a vertical load is applied, both grating pitches will be elongated due to a Poisson's ratio deformation orthogonal to the applied loading, and there should be an increasing shift in Bragg wavelength $\lambda_B$.

Figure 8:
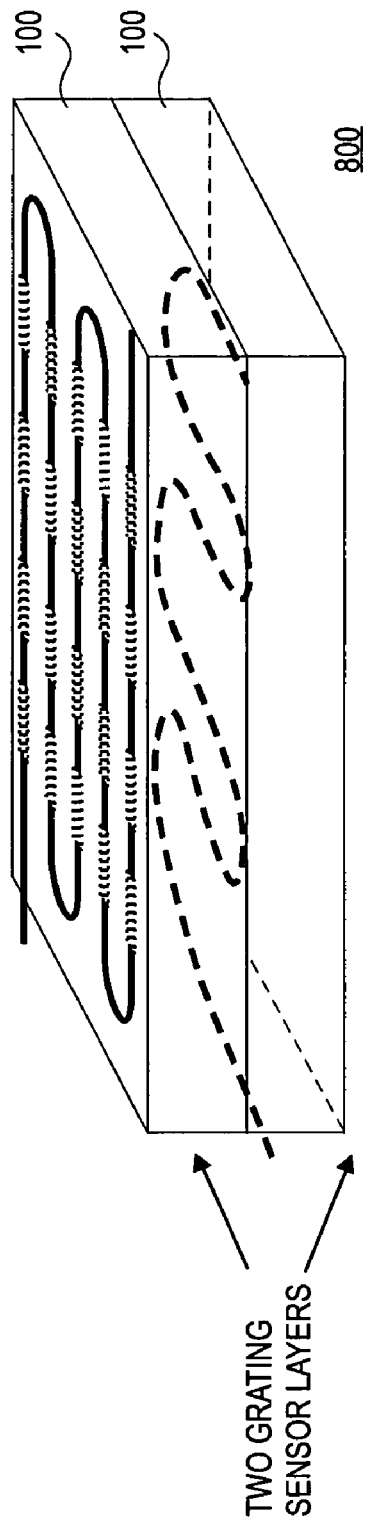
FIGS. 8 and 9 are cross-section diagrams of a pressure and shear stress sensor according to embodiments of the present invention.
Figure 9:
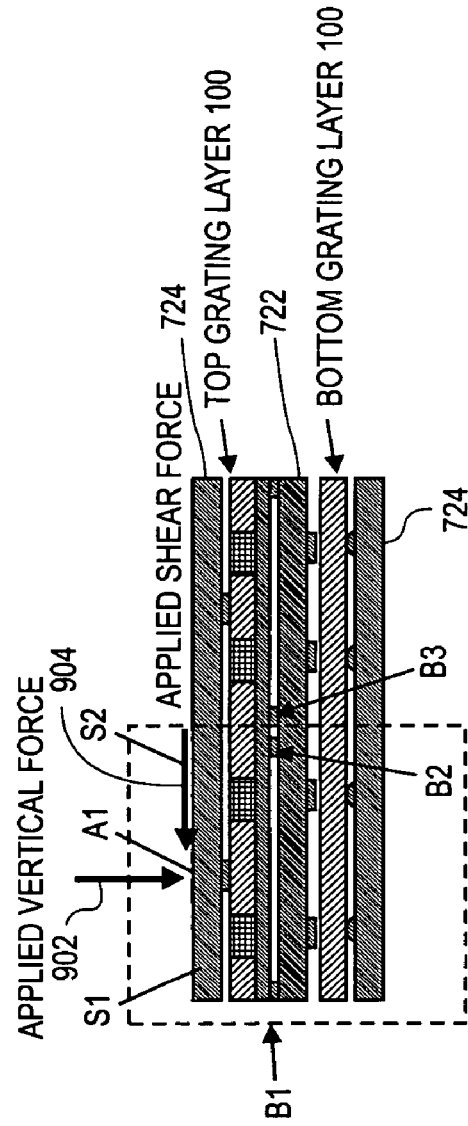

In embodiments of the present invention, two distributive pressure sensors 100 may be used to fabricate a shear sensor according to embodiments of the present invention. For example, after constructing another distributive pressure sensor 100 and another bottom support 724, in a block 620, the second distributive pressure sensor 100 and second bottom support 724 are then laminated to the top support structure 722 to complete a final pressure and shear stress sensor 800 (FIG. 8). In the pressure and shear stress sensor 800 the two pressure sensors 100 disposed on top of each other so the parallel rows of waveguides of the top and bottom planes are perpendicular or orthogonal to one another. The two supporting structures 722 and 724 may be used to decouple the simultaneous shear and pressure components.

The applied shear is proportional to the difference of the strain obtained by S1 and S2. When shear force is applied along the axial direction as indicated by the arrow 904, one grating will be under compression and the other will be under tension since the bottom support (B1, B2, and B3) of each element prevents the gratings from sliding forward. The resulting Bragg wavelength shift $\Delta\lambda_B$ may have one Bragg wavelength $\lambda_B$ going up and the other Bragg wavelength $\lambda_B$ going down. The shear measurement of the entire sensing area may be derived from the axial shear measurement of the two Bragg grating planes. In another embodiment, the derivation may be accomplished by measuring the shear component based on the relative change in the load position on the pressure points between the top and bottom sensor layers. Because the initial loading position is known, shear can be derived from the relative load position change on the lower sensor layer after a shear load has been applied. Temperature compensation is automatic, as wavelength change due to temperature variations will be the same for all gratings.

There are advantages of pressure and shear sensors fabricated and operated according to embodiments of the present invention. First, because of the fabrication process 600, it makes the integration of sensors, light source, and detectors on a single "sheet of flexible material" possible. The integration reduces the overall size and the power consumption of the system, while improving the signal to noise ratio and image resolution. The proposed batch process 600 also enables the entire system to be constructed in one process. Batch processing also guarantees a more consistent product, low cost in manufacturing and makes a moldable, flexible, conformable, and deformable pressure and shear measuring devices possible.

The operations of the process 600 are described as multiple discrete blocks performed in turn in a manner that is most helpful in understanding embodiments of the invention. However, the order in which they are described should not be construed to imply that these operations are necessarily order dependent or that the operations be performed in the order in which the blocks are presented. Of course, the process 600 is only an example process and other processes may be used to implement embodiments of the present invention. A machine-accessible medium with machine-readable instructions thereon may be used to cause a machine (e.g., a processor) to perform the process 600.

FIG. 10 is cross-section views of stages of fabrication of a pressure sensor 1000 according to alternative embodiments of the present invention.

Figure 10A:
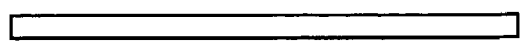
FIG. 10 is cross-section views of stages of fabrication of a pressure sensor according to alternative embodiments of the present invention.

FIG. 10(a) shows the silicon substrate.

Figure 10B:

FIG. 10(b) shows the Ultra-i123 photoresist coated on the silicon.

Figure 10C:
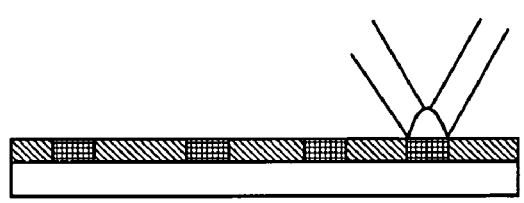

FIG. 10(c) shows the grating being formed in the Ultra-i123 photoresist. In one embodiment, the grating may be formed in the Ultra-i123 photoresist using holography, electron beam lithography, or other suitable technique, such as by using a phase mask, for example. In the illustrated embodiment, the grating is formed in the Ultra-i123 photoresist using a two beam interference technique.

Figure 10D:
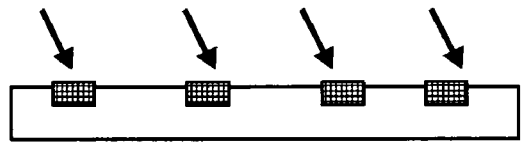

FIG. 10(d) shows the unwanted Ultra-i123 photoresist etched away. In one embodiment, the etching may be accomplished using an inductive coupling plasma (ICP) process.

Figure 10E:

FIG. 10(e) shows a coating of SU-8 photoresist on the gratings and silicon substrate. In one embodiment, the coating of SU-8 may be spin-coated onto the gratings and substrate. Contact photolithography may be used to create the waveguide. The gratings and waveguide mold may be made after developing.

Figure 10F:
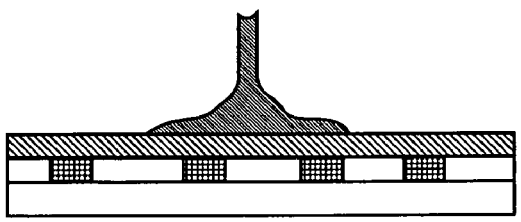

FIG. 10(f) shows cured PDMS on the substrate and gratings. The PDMS forms the waveguide core layer. In one embodiment, the PDMS is spin coated.

Figure 10G:
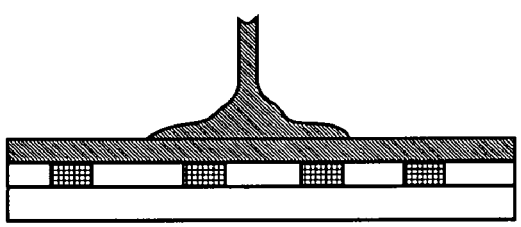
Figure 10H:
Figure 10I:
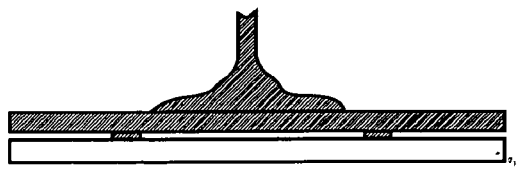
Figure 10J:
Figure 10K:
Figure 10L:
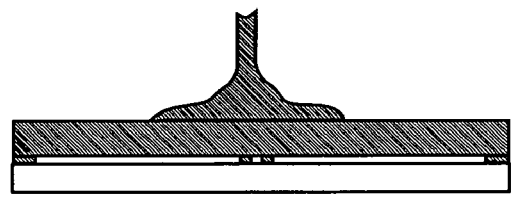
Figure 10M:
Figure 10N:
Figure 10O:
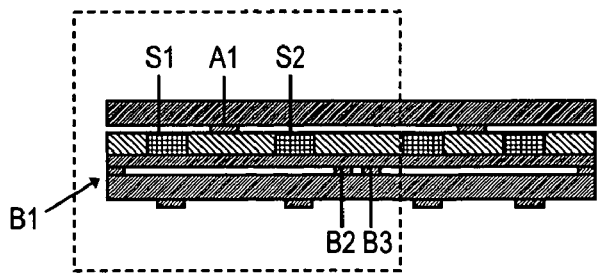

FIG. 10(g) shows another layer of PDMS on the first layer of PDMS. The second layer of PDMS may have a different index of refraction than the cladding layer on top of the PDMS core layer.

FIGS. 10(h)-10(n) substantially mirror FIGS. 7(h)-7(n).

Figure 11:
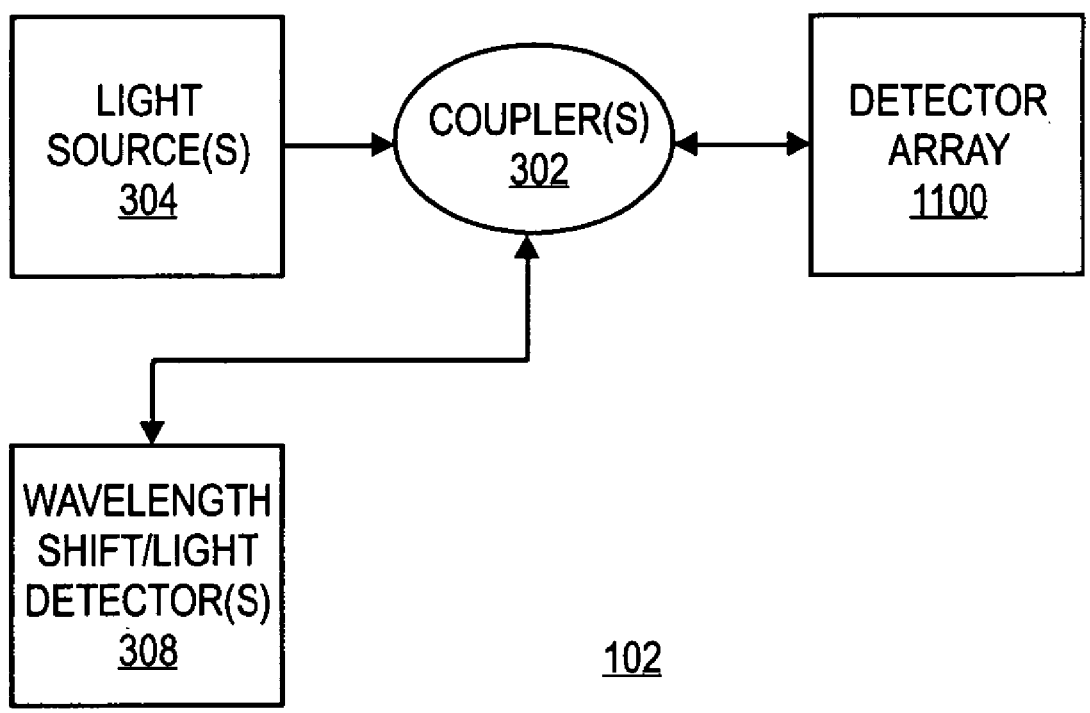
FIG. 11 is a high-level block diagram of a sensor according to an embodiment of the present invention.

In alternative embodiments, rather than having Bragg gratings disposed on the two flexible layers of a pressure and shear stress sensor, other detectors may be employed. For example, each flexible layer may have piezoelectric detectors, capacitive sensors, or other suitable means for responding to an applied load. FIG. 11 is a high-level block diagram of a sensor according to an embodiment of the present invention. The sensor includes one or more couplers 302, one or more light sources 304, one or more wavelength shift/light detectors 308, and a detector array 1100 disposed in or on the flexible substrate 102. In embodiments of the present invention, the detector array may include a piezoelectric detector array, a capacitive sensors array, or other suitable array of detectors.

Embodiments of the present invention may be used in medical applications. For example, annual diabetic foot infection related costs to hospitals around $550 million, yet annual diabetic foot infection is not an area of current research and development focus. Pressure and shear sensors fabricated and operated according to embodiments of the present invention can be used as in-shoe sole or mat-based gait systems to prevent and monitor the development of the diabetic foot. The flexible distributed pressure and shear sensor can also be used in prosthetic arms or legs to monitor the pressure profiles on the joints and the prosthetic socket. The flexible distributed pressure and shear sensor can also be used as a sole sensor for artificial legs where the flexible distributed pressure and shear sensor can provide ground profile information. The flexible distributed pressure and shear sensor can also be use as a product development sensor for evaluating the wheelchair seat, crutches.

Embodiments of the present invention may be used in dental applications such as bite sensors and orthopedic gait analysis. For example, the flexible distributed pressure and shear sensor may be used in a system for measuring three-dimensional profiles of dental casts and three-dimensional tooth movement during orthodontic treatment.

Embodiments of the present invention may be used in civil and infrastructure applications. For example, the flexible distributed pressure and shear sensor may be used in monitoring of wear-and-tear of buildings, highway systems, bridges and dams.

Embodiments of the present invention may be used in robotic applications. For example, the flexible distributed pressure and shear sensor may be used as tactile and shear sensors for robotic arms. The flexible distributed pressure and shear sensor may be used to create force feedback or sensing motion. The flexible distributed pressure and shear sensor may be used to create artificial skin for tactile and display purposes.

Embodiments of the present invention may be used in commercial applications. For example, the flexible distributed pressure and shear sensor may be suitable for sports equipment for active support (change vertical support stiffness and side support), embedded sensors for gloves, bats, clubs, hats, shoes, etc., feedback to enhance training of athletes, smart clothes (e.g. reduce drag), product development, such as monitoring horizontal motion, shifting of pressure, increase comfort and decrease fatigue, a bicycle seat sensor, tire sensors, helmet sensors (create a better fit to the profile of the head), and/or as a touch-screen pad.

Embodiments of the present invention may be used with wireless data acquisition. For example, the flexible distributed pressure and shear sensor may be used in a low cost commercial wireless serial transceiver that allows for easy data acquisition by remote systems and real-time relaying of raw data handled primarily by a microcontroller located on the flexible distributed pressure and shear sensor and analogue systems.

As described above, embodiments of the present invention may be implemented using hardware, software, or a combination thereof. In implementations using software, the software may be stored on a machine-accessible medium. A machine-accessible medium includes any mechanism that may be adapted to store and/or transmit information in a form accessible by a machine (e.g., a computer, network device, personal digital assistant, manufacturing tool, any device with a set of one or more processors, etc.). For example, a machine-accessible medium includes recordable and non-recordable media (e.g., read only memory (ROM), random access memory (RAM), magnetic disk storage media, optical storage media, flash memory devices, etc.), as recess as electrical, optical, acoustic, or other form of propagated signals (e.g., carrier waves, infrared signals, digital signals, etc.).

In the above description, numerous specific details, such as, for example, particular processes, materials, devices, and so forth, are presented to provide a thorough understanding of embodiments of the invention. One skilled in the relevant art will recognize, however, that the embodiments of the present invention may be practiced without one or more of the specific details, or with other methods, components, etc. In other instances, structures or operations are not shown or described in detail to avoid obscuring the understanding of this description.

Reference throughout this specification to "one embodiment" or "an embodiment" means that a particular feature, structure, process, block, or characteristic described in connection with an embodiment is included in at least one embodiment of the present invention. Thus, the appearance of the phrases "in one embodiment" or "in an embodiment" in various places throughout this specification does not necessarily mean that the phrases all refer to the same embodiment. The particular features, structures, or characteristics may be combined in any suitable manner in one or more embodiments.

The terms used in the following claims should not be construed to limit embodiments of the invention to the specific embodiments disclosed in the specification and the claims. Rather, the scope of embodiments of the invention is to be determined entirely by the following claims, which are to be construed in accordance with established doctrines of claim interpretation.

What is claimed is:

1. An apparatus, comprising:
a shear stress sensor having:
   a first sensor having:
      a first flexible substrate; and
      a first detector array disposed in or on the first flexible substrate along a first series path, wherein the first series path includes a first input and a first output;
   a second sensor having:
      a second flexible substrate; and
      a second detector array disposed in or on the second flexible substrate along a second series path, wherein the second series path includes a second input and a second output,
   wherein the first sensor is disposed on the second sensor, and
   wherein the first series path is disposed perpendicular to the second series path.

2. The apparatus of claim 1, wherein the first detector array comprises piezoelectric sensors.

3. The apparatus of claim 1, wherein the first detector array comprises capacitive sensors.

4. The apparatus of claim 1, wherein the first detector array comprises Bragg gratings.

5. The apparatus of claim 4, wherein the first and second series paths comprise first and second waveguides, respectively.

6. A method, comprising:
forming a first waveguide on a first flexible optical medium;
forming a first Bragg grating array in the first waveguide;
forming a second waveguide on a second flexible optical medium;
forming a second Bragg grating array in the second waveguide;
disposing the first flexible optical medium on the second optical medium;
constructing two molds of an interference pattern on two silicon substrates;
spinning a first photoresist on the silicon substrates;
writing a Bragg grating pattern on the first photoresist on the two silicon substrates;
developing the first photoresist;
transferring the Bragg grating pattern from the molds to two pieces of flexible optical material, and the Bragg grating pattern having perturbations with spaces therebetween, the two pieces of flexible optical material having a first index of refraction;
spin-coating a second optical material onto the two pieces of flexible optical material to substantially fill the grating spaces, the second optical material having a second index of refraction different from the first index of refraction;
etching away a portion of the second optical material; and
patterning the first and waveguides in the second optical material.

7. The method of claim 6, further comprising:
forming a top support layer and bottom support layer for each of the two pieces of flexible optical material; and
laminating together the top support layer and bottom support layer for each of the two pieces of flexible optical material and the two pieces of flexible optical material.

* * * * *